(12) United States Patent
Ono

(10) Patent No.: US 8,356,898 B2
(45) Date of Patent: Jan. 22, 2013

(54) FUNDUS CAMERA AND OPHTHALMOLOGIC IMAGE PROCESSING APPARATUS

(75) Inventor: Shigeaki Ono, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 106 days.

(21) Appl. No.: 12/967,503

(22) Filed: Dec. 14, 2010

(65) Prior Publication Data

US 2011/0141436 A1 Jun. 16, 2011

(30) Foreign Application Priority Data

Dec. 16, 2009 (JP) ................. 2009-285764

(51) Int. Cl.
*A61B 3/14* (2006.01)
*A61B 3/10* (2006.01)
(52) U.S. Cl. ......... 351/206; 351/208; 351/210; 351/221
(58) Field of Classification Search ........... 351/200–246
See application file for complete search history.

(56) References Cited

U.S. PATENT DOCUMENTS

| 7,556,379 | B2* | 7/2009 | Dobashi | 351/221 |
| 7,731,361 | B2* | 6/2010 | Honda | 351/211 |
| 7,824,035 | B2* | 11/2010 | Yamada et al. | 351/206 |
| 7,905,597 | B2* | 3/2011 | Tsukada et al. | 351/206 |

FOREIGN PATENT DOCUMENTS

| JP | 2000-107133 A | 4/2000 |
| JP | 2003-52639 A | 2/2003 |

* cited by examiner

*Primary Examiner* — Mohammed Hasan
(74) *Attorney, Agent, or Firm* — Canon U.S.A., Inc., IP Division

(57) ABSTRACT

A fundus camera includes an imaging unit configured to capture a fundus image formed via a photographic optical system, a portion information detection unit configured to detect information about a predetermined portion of a fundus from image data acquired from the imaging unit, and an image generation unit configured to generate an image according to a tone curve which is changed according to a result of a detection performed by the portion information detection unit of the fundus image.

10 Claims, 11 Drawing Sheets

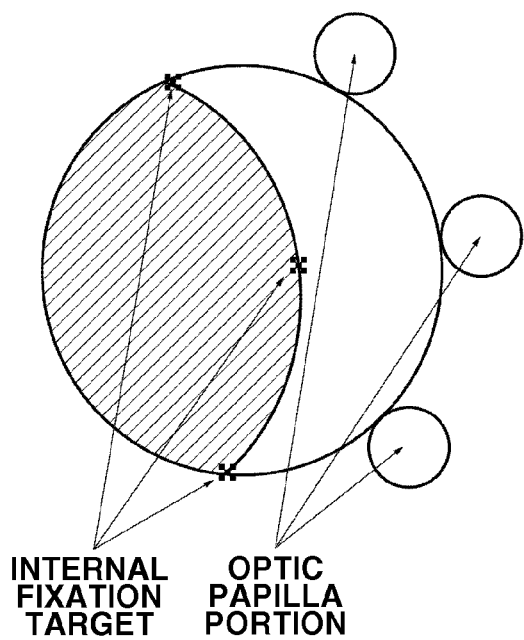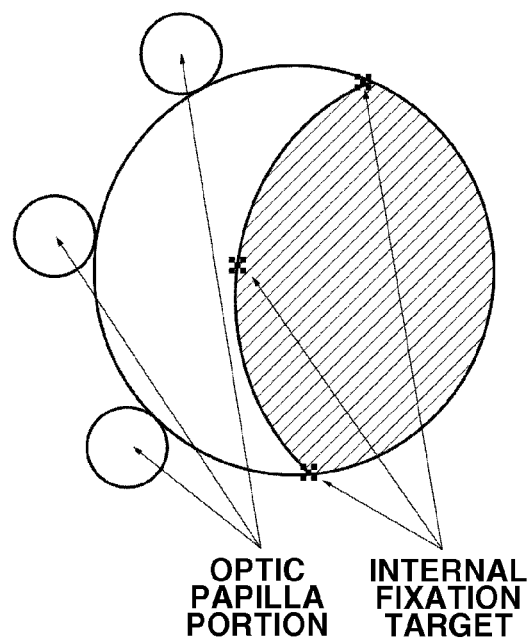
FIG.3A
RIGHT EYE
FIG.3B
LEFT EYE
INTERNAL FIXATION TARGET  OPTIC PAPILLA PORTION
OPTIC PAPILLA PORTION  INTERNAL FIXATION TARGET

INTERNAL
FIXATION
TARGET

FOCUS
INDEX

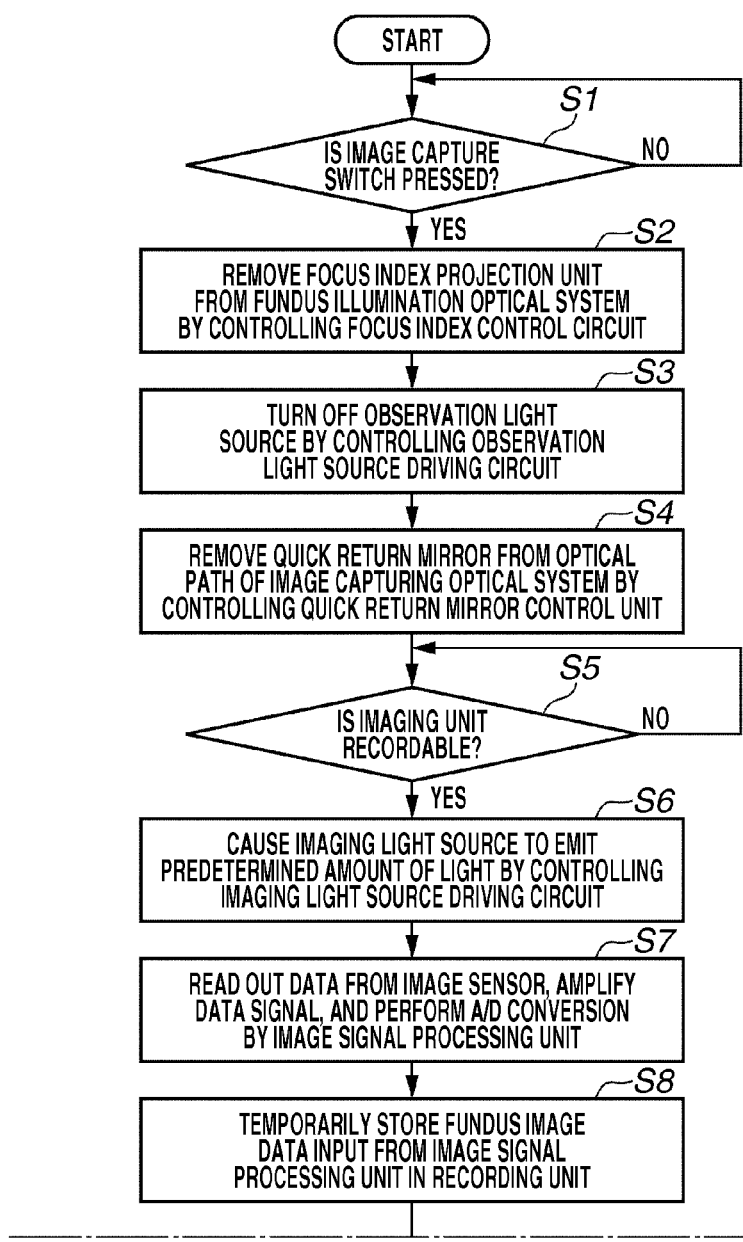

INTERNAL
FIXATION TARGET

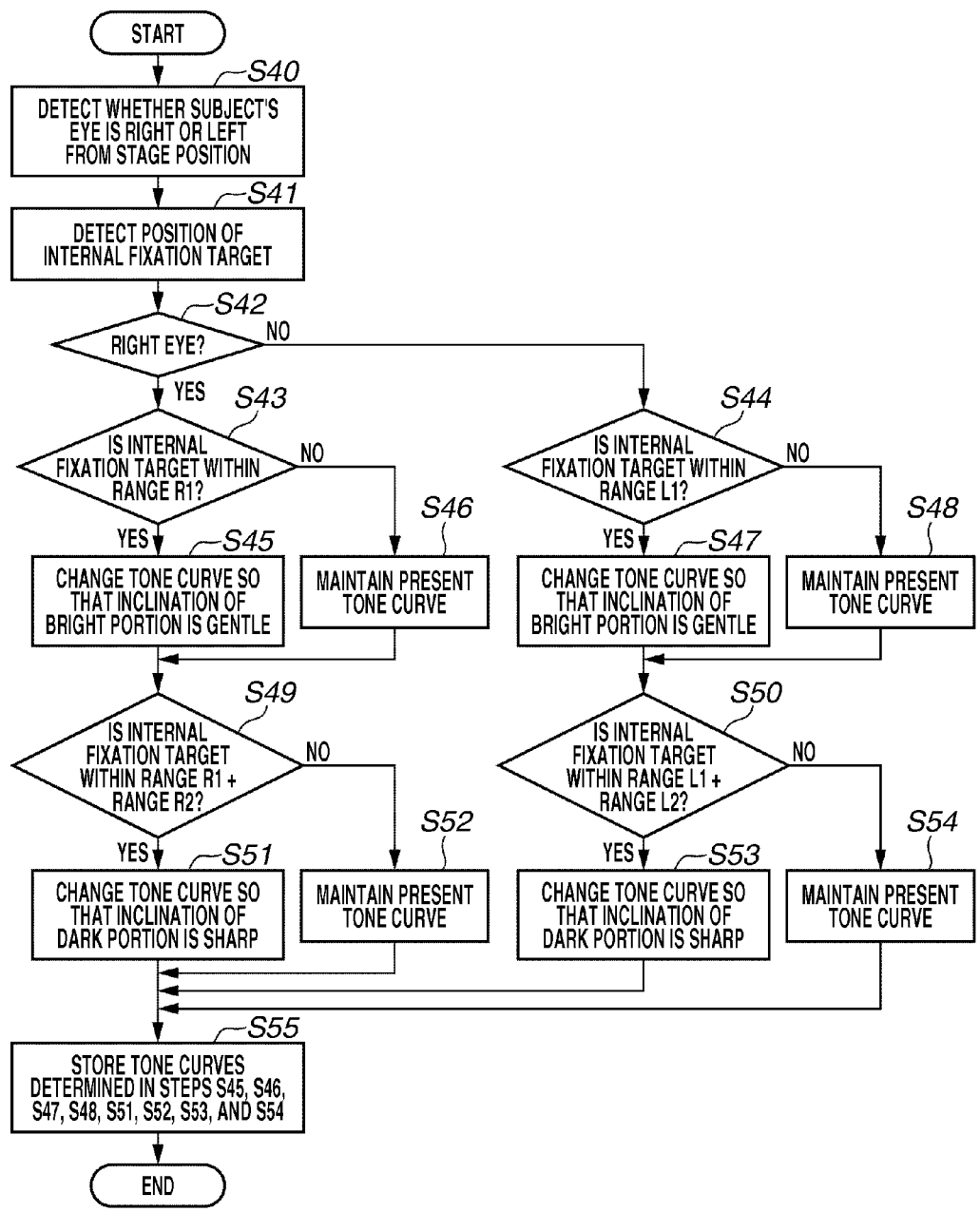

FUNDUS CAMERA AND OPHTHALMOLOGIC IMAGE PROCESSING APPARATUS

BACKGROUND OF THE INVENTION

1. Field of the Invention

The present invention relates to a fundus camera and an ophthalmologic image processing apparatus. More particularly, the present invention relates to a technique useful for gradation conversion of an eye fundus image.

2. Description of the Related Art

When an image of a fundus of a subject's eye is captured using a fundus camera, it is useful if both an optic papilla portion and a macular portion, which are the brightest and the darkest portions in a fundus image, can be observed at the same time.

Japanese Patent Application Laid-Open No. 2000-107133 discusses a fundus camera that captures an image of a subject's eye using an imaging unit by alternately changing an intensity of light emitted from a photographing light source.

Japanese Patent Application Laid-Open No. 2003-52639 discusses a fundus camera that generates a high-contrast image for each region of interest, such as a macular portion or an optic papilla portion, in one image-capturing operation of a fundus according to a setting value for each region, and stores the generated image.

However, if the conventional fundus camera is used to capture one eye fundus image including both the optic papilla portion being the brightest portion and the macular portion being the darkest portion in the fundus image, since an image sensor does not provide a satisfactory dynamic range, the macular portion will be underexposed if the exposure of the optic papilla portion is appropriate. On the other hand, overexposure of the optic papilla portion occurs if the exposure of the macular portion is appropriate.

If a fundus camera such as the one discussed in Japanese Patent Application Laid-Open No. 2000-107133 is used, an operator needs to flash the photographing light source twice in capturing an image.

If a fundus camera such as the one discussed in Japanese Patent Application Laid-Open No. 2003-52639 is used, the operator needs to look at two different images when the operator views the optic papilla portion and the macular portion.

SUMMARY OF THE INVENTION

The present invention is directed to a mechanism capable of acquiring an image which includes both an optic papilla portion and a macular portion with appropriate gradation for diagnosis.

According to an aspect of the present invention, a fundus camera includes an imaging unit configured to capture a fundus image formed via a photographic optical system, a portion information detection unit configured to detect information about a predetermined portion of a fundus from image data acquired from the imaging unit, and an image generation unit configured to generate an image according to a tone curve which is changed according to a result of a detection performed by the portion information detection unit of the fundus image.

According to an exemplary embodiment of the present invention, a mechanism for acquiring an image including both an optic papilla portion and a macular portion with appropriate gradation for diagnosis can be provided.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 3A and 3B illustrate a movement range of a lighting index of an internal fixation target.

FIGS. 6A and 6B are a flowchart illustrating an operation of a calculation unit according to the first exemplary embodiment.

FIG. 9 is a flowchart illustrating an operation of a calculation unit according to a third exemplary embodiment of the present invention.

DESCRIPTION OF THE EMBODIMENTS

Various exemplary embodiments, features, and aspects of the invention will be described in detail below with reference to the drawings.

The present invention will be described according to exemplary embodiments described with reference to FIGS. 1 to 9.

Figure 1:
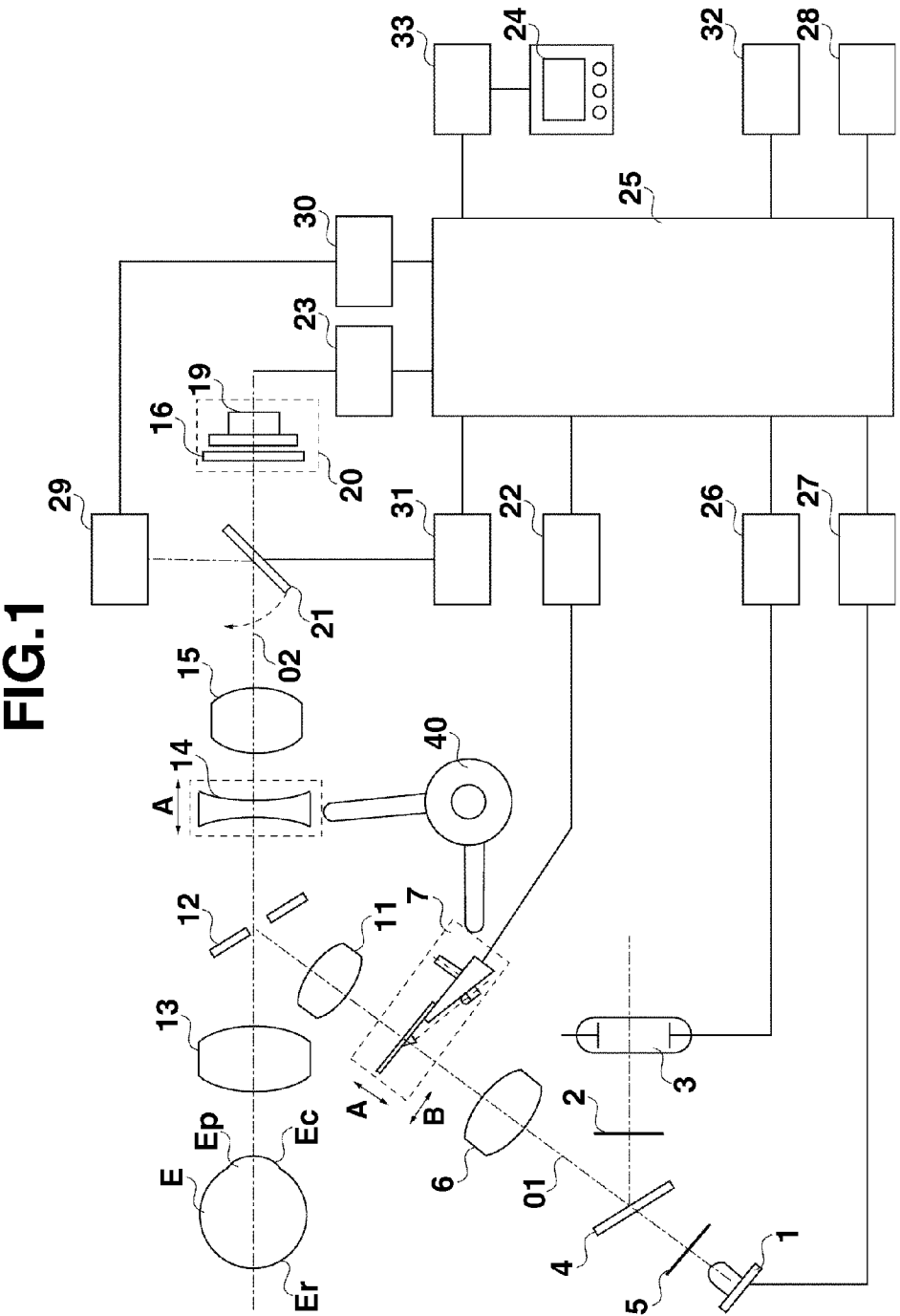
FIG. 1 illustrates a configuration of a fundus camera according to a first exemplary embodiment of the present invention.

FIG. 1 illustrates a configuration of a fundus camera according to a first exemplary embodiment. Along an optical path from an observation light source 1 to an objective lens 13, there are arranged a diaphragm 5 including a ring-shaped aperture, a mirror 4, a relay lens 6, a focus index projection unit 7, a relay lens 11, and a perforated mirror 12 in this order. These components constitute a fundus illumination optical system 01. The observation light source 1 includes a light-emitting diode (LED) showing wavelength characteristics in the near-infrared region.

Along an optical path in a reflection direction of the mirror 4, there are arranged a photographing light source 3 being a flash and a diaphragm 2 including a ring-shaped aperture in this order. The mirror 4 is a dichroic mirror. The mirror 4 transmits near-infrared light and reflects visible light.

Figure 2A:
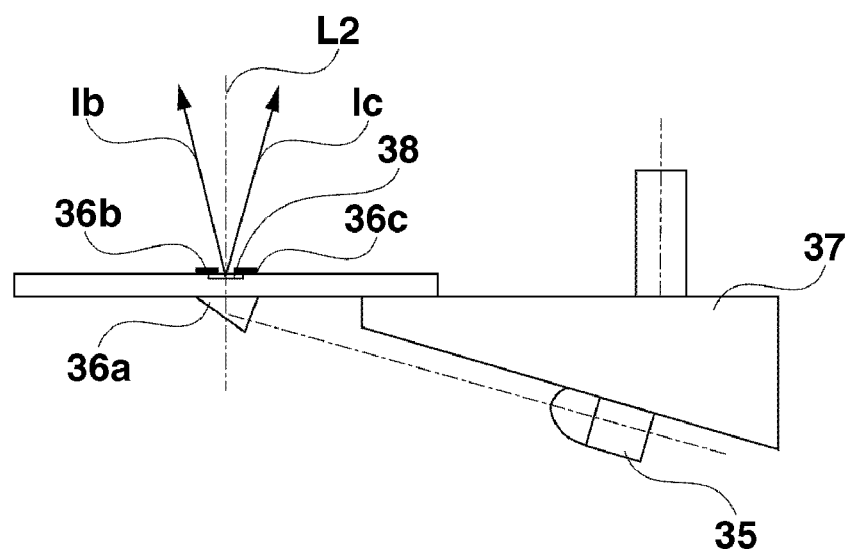
FIGS. 2A and 2B illustrate details of a focus index projection unit.
Figure 2B:
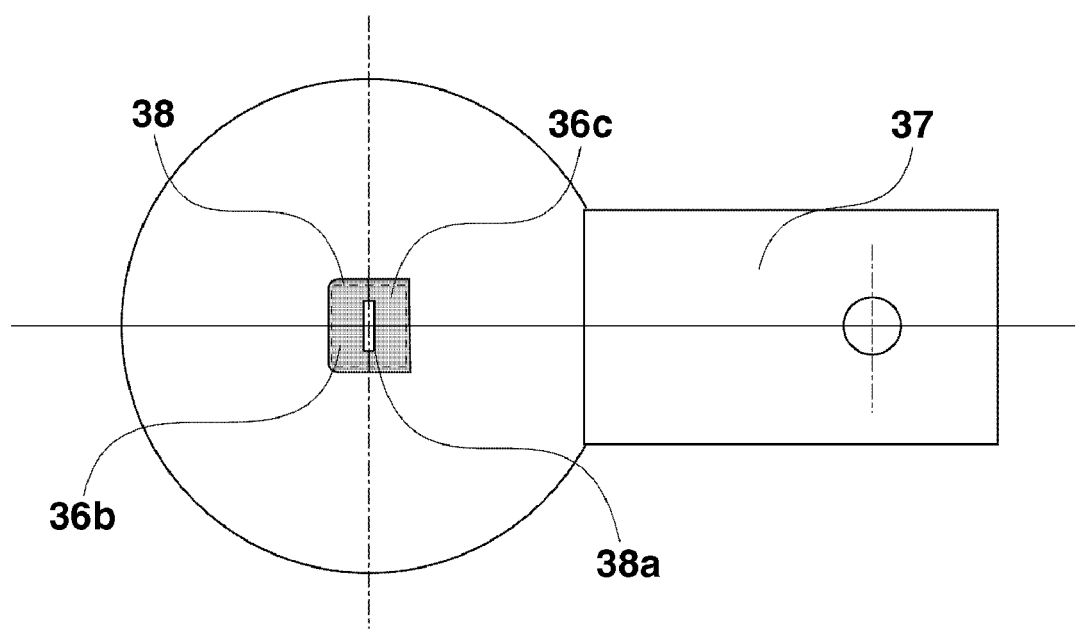

As illustrated in FIG. 2A, the focus index projection unit 7 includes a focus split prism 36, a focus index 38, and a focus index light source 35. The focus split prism 36 includes prism portions 36a, 36b, and 36c. The focus index 38 includes a rectangular aperture portion. According to a focus link mechanism 40, the focus index projection unit 7 and a focusing lens 14 are operated in an interlocking manner in a direction "A" illustrated in FIG. 1 such that an image sensor 19 of an imaging unit 20 optically conjugates with the focus index 38 of the focus index projection unit 7. Further, when an operator captures a still image, the focus index projection unit 7 moves in a direction B illustrated in FIG. 1 and is retracted from the fundus illumination optical system 01.

On an optical path of the perforated mirror 12 in the transmission direction, there are arranged the focusing lens 14, a photographic lens 15, a quick return mirror 21, and the imaging unit 20. These components constitute a fundus photographic optical system 02.

In the reflection direction of the quick return mirror 21, there is arranged an internal fixation target 29. The internal fixation target 29 is optically conjugate with the image sensor 19 of the imaging unit 20. The quick return mirror 21, which is a dichroic mirror, transmits infrared light and reflects visible light. Further, when a still image is captured, the quick return mirror 21 moves in a direction indicated by an arrow illustrated in FIG. 1. Accordingly, the quick return mirror 21 is retracted from the fundus photographic optical system 02.

The imaging unit 20 includes the image sensor 19 and a trichromatic wavelength resolution unit 16. An output from the imaging unit 20 is connected to an image signal processing unit 23 and further to a calculation unit 25. The calculation unit 25 includes a central processing unit (CPU) 1010 (not shown) and performs overall control of the fundus camera using a computer-executable program and pieces of data stored in a random access memory (RAM) or a read-only memory (ROM). Further, the calculation unit 25 can execute predetermined calculation processing by executing the computer-executable program. Further, the calculation unit 25 includes a portion information detection unit 251, an image generation unit 252, and a right-and-left detection unit 253, which are not illustrated.

The portion information detection unit 251 determines whether a macular portion or an optic papilla portion, as a predetermined portion, is included in an eye fundus image. The portion information detection unit 251 also determines whether a macular portion or an optic papilla portion is included in an eye fundus image according to a position of a lighting index of the internal fixation target 29 and left/right eye information.

The image generation unit 252 generates an image according to a tone curve which is changed according to a detection result output from the portion information detection unit 251.

The observation light source 1, a photographing light source 2, the focus index projection unit 7, a display unit 24, the quick return mirror 21, and the internal fixation target 29 are connected to an observation light source driving circuit 27, a photographing light source driving circuit 26, a focus index control circuit 22, a display unit control unit 33, a quick return mirror control unit 31, and an internal fixation target control unit 30, respectively. The observation light source driving circuit 27, the photographing light source driving circuit 26, the focus index control circuit 22, the display unit control unit 33, the quick return mirror control unit 31, and the internal fixation target control unit 30 are connected to the calculation unit 25.

Now, an operation performed when an operator observes a fundus will be described.

The calculation unit 25 drives the observation light source driving circuit 27 so as to turn on the observation light source 1 and control an amount of light thereof. The light flux emitted from the observation light source 1 passes through the diaphragm 5 including a ring-shaped aperture, the mirror 4, the relay lens 6, the focus index projection unit 7, and the relay lens 11. Then, the light flux is reflected by a portion in the periphery of the perforated mirror 12. After then, the reflected light passes through the objective lens 13, and a cornea Ec and a pupil Ep of a subject's eye E, and illuminates a fundus Er thereof.

The calculation unit 25 controls the focus index control circuit 22 to turn on the focus index light source 35. In FIG. 2A, the light flux emitted from the focus index light source 35 is deflected in a direction of an optical axis L2 by the prism portion 36a of the focus split prism 36, and is incident on the prism portions 36b and 36c. The prism portions 36b and 36c include prism faces that form symmetric angles with respect to the optical axis L2. The light flux that is incident on the prism portions 36b and 36c passes through a rectangular aperture portion 38a of the focus index 38 illustrated in FIG. 2B. Then, the light flux is separated into two focus index light flux lb and lc which are symmetric with respect to the optical axis L2. Then, the focus index light flux lb and lc are incident on the subject's eye E after passing through the relay lens 11, the perforated mirror 12, and the objective lens 13.

Figure 4A:
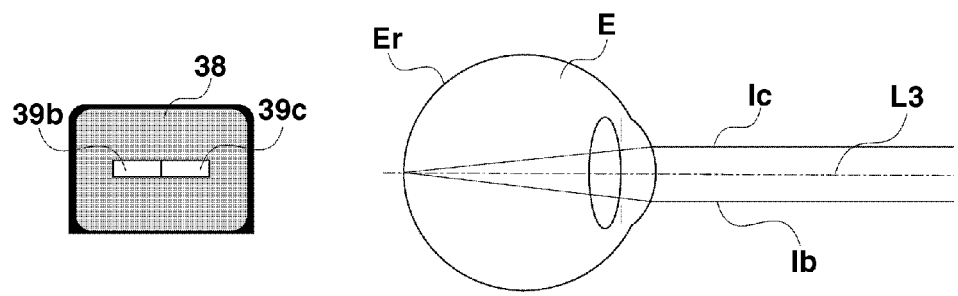
FIGS. 4A to 4C illustrate a focus index light flux directed onto a fundus of a subject's eye and focus index images formed on the fundus according to the focus index light flux.
Figure 4B:
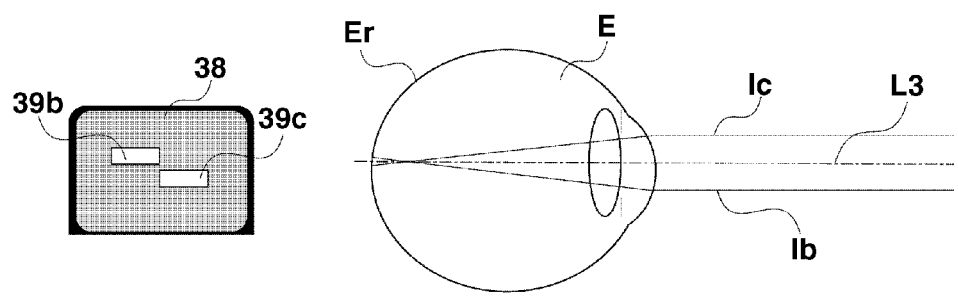
Figure 4C:
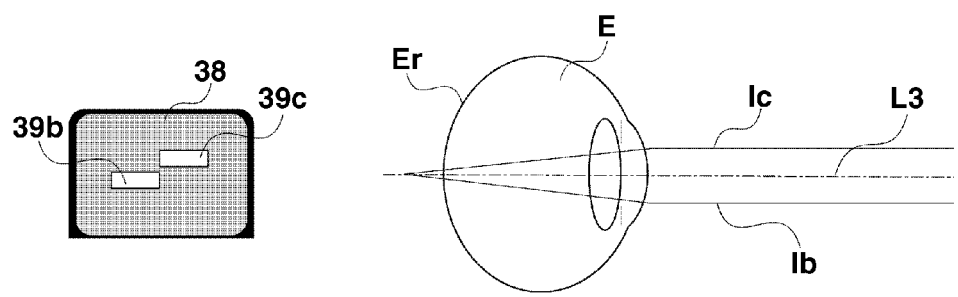

FIGS. 4A to 4C illustrate the focus index light flux lb and lc directed onto the fundus Er of the subject's eye E and focus index images 39b and 39c formed on the fundus Er according to the focus index light flux lb and lc.

FIG. 4A illustrates a case where the fundus Er of the subject's eye E is optically conjugate with the focus index 38. Since the fundus Er is optically conjugate with the focus index 38, the two separated focus index light flux lb and lc form the focus index images 39b and 39c of the rectangular aperture portion 38a of the focus index 38 illustrated in FIG. 4A on the fundus Er. The focus index images 39b and 39c are formed in a line.

FIG. 4B illustrates a case where the subject's eye E is nearsighted compared to the case illustrated in FIG. 4A. In this case, since the fundus Er is not optically conjugate with the focus index 38, the two separated focus index light flux lb and lc form the focus index images 39b and 39c of the rectangular aperture portion 38a of the focus index 38 illustrated in FIG. 4B on the fundus Er. The focus index images 39b and 39c are shifted in a vertical direction. More specifically, the image 39b is upwardly shifted and the image 39c is downwardly shifted.

FIG. 4C illustrates a case where the subject's eye E is farsighted compared to the case illustrated in FIG. 4A. Since the fundus Er is not optically conjugate with the focus index 38, the two separated focus index light flux lb and lc form the focus index images 39b and 39c of the rectangular aperture portion 38a of the focus index 38 illustrated in FIG. 4C on the fundus Er. The focus index images 39b and 39c are shifted in a vertical direction. More specifically, the image 39b is downwardly shifted and the image 39c is upwardly shifted. The focus index light source 35 includes a light-emitting diode (LED) having the center wavelength in the near-infrared region.

The calculation unit 25 turns on the internal fixation target 29 by controlling the internal fixation target control unit 30 so that the index is projected on the fundus. Since the internal fixation target is visible light, it is reflected by the quick return mirror 21. Then the reflected light is projected on the fundus Er after passing through the photographic lens 15, the focusing lens 14, holes of the perforated mirror 12, the objective lens 13, the cornea Ec, and the pupil Ep of the subject's eye E. According to position information of the internal fixation target input by the operator using an input unit 32, the calculation unit 25 changes a lighting position of the internal fixation target 29 by controlling the internal fixation target control unit 30. Thus, the fixation of the subject's eye can be guided according to the change in the lighting position of the internal fixation target 29.

The illuminated fundus image and the focus index image pass through the pupil Ep and the cornea Ec of the subject's eye E, and also the objective lens 13 as the imaging optical system and the holes of the perforated mirror 12. Then, via the focusing lens 14 and the photographic lens 15, and further, bypassing through the trichromatic wavelength resolution unit 16 in the imaging unit 20, the images are formed on the image sensor 19.

The image sensor 19 performs photoelectric conversion of the fundus image and the focus index image that have been formed thereon. The image signal processing unit 23 reads out data from the image sensor 19, amplifies the data signal, and performs analog-to-digital (A/D) conversion of the signal. Accordingly, digital image data is generated. When the generated digital image data is input in the calculation unit 25, according to the control of the display unit control unit 33, the digital data is simultaneously converted into moving image data which is to be displayed on the display unit 24. Further, the lighting position of the internal fixation target 29 is superimposed as a character and displayed on the display unit 24. An example of this image is illustrated in FIG. 5A.

The operator observes the focus index images 39b and 39c of the rectangular aperture portion 38a of the focus index 38 displayed on the display unit 24 and operates a focus knob (not shown) so that the focus index images 39b and 39c are aligned in a straight line. In this way, the fundus Er will be optically conjugate with the focus index 38. Since the focus index 38 of the focus index projection unit 7 is optically conjugate with the image sensor 19 by the focus link mechanism 40, the fundus Er is optically conjugate with the image sensor 19. Accordingly, the fundus Er will be in focus.

Figure 6B:
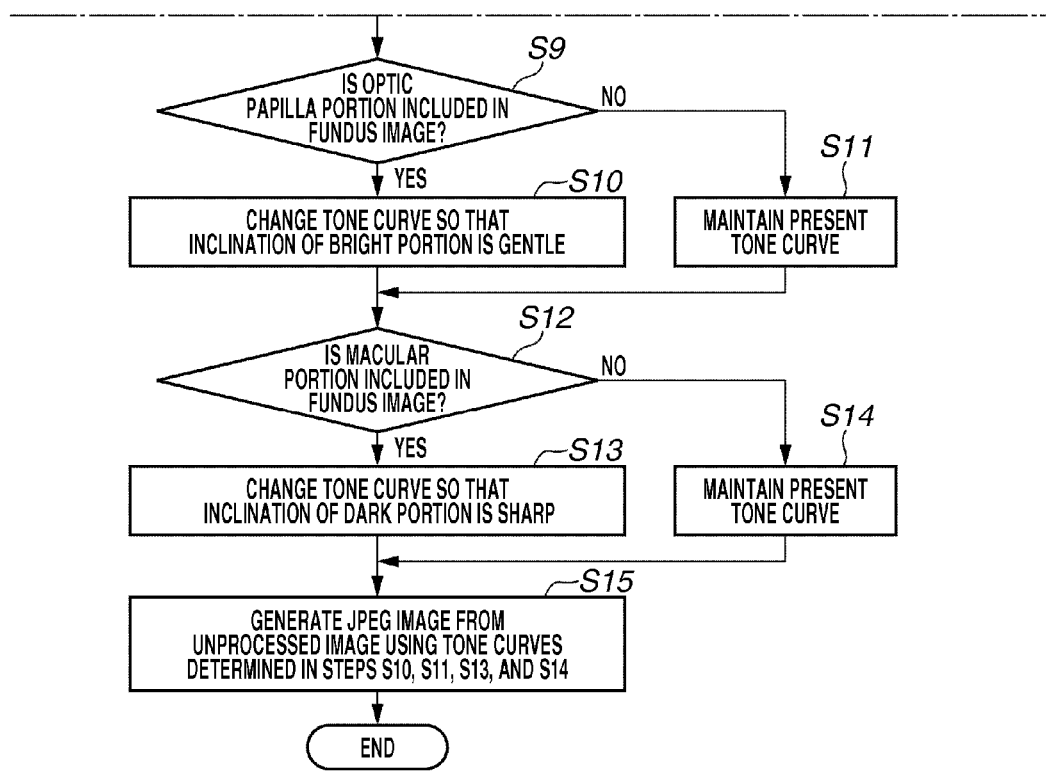

Next, the fundus image capturing operation will be described with reference to the flowchart illustrated in FIGS. 6A and 6B.

Figure 5A:
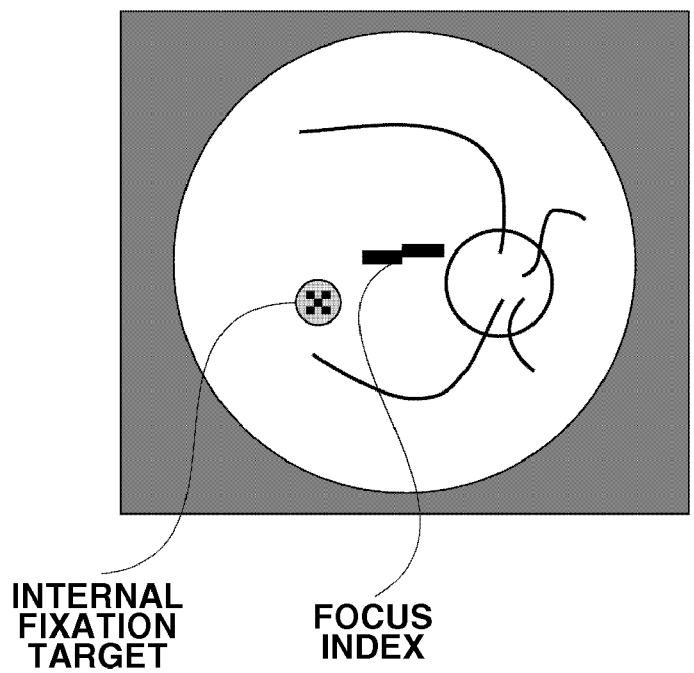
FIG. 5A illustrates a display screen of a display unit according to the first exemplary embodiment.

The operator adjusts an alignment position and the focus while viewing the image displayed on the display unit 24 as illustrated in FIG. 5A. When the alignment and the focusing are adjusted, the operator pushes an image capturing switch (not shown) included in the input unit 32. Accordingly, in step 51, the calculation unit 25 detects that the image capturing switch has been pushed. In step S2, the calculation unit 25 moves the focus index projection unit 7 out of the optical path in the direction B by controlling the focus index control circuit 22.

In step S3, the calculation unit 25 turns off the observation light source 1 by controlling the observation light source driving circuit 27. In step S4, the calculation unit 25 moves the quick return mirror 21 out of the optical path of the photographic optical system 02 by controlling the quick return mirror control unit 31.

In step S5, the calculation unit 25 confirms whether the imaging unit 20 is in a recordable state. If the imaging unit 20 is in the recordable state (YES in step S5), the processing proceeds to step S6. If the imaging unit 20 is not in the recordable state (NO in step S5), step S5 is repeated. In step S6, the calculation unit 25 controls the photographing light source driving circuit 26 in synchronization with the imaging unit 20 so that a predetermined amount of light is emitted from the photographing light source 3.

In step S7, the image signal processing unit 23 reads out data from the image sensor 19, amplifies the data signal, and performs A/D conversion of the signal. Then, the converted data is input in the calculation unit 25 as unprocessed data of a digital fundus image. In step S8, the input data is temporarily stored in a recording unit 28.

In step S9, the portion information detection unit 251 reads out the unprocessed image temporarily stored in the recording unit 28 and detects whether an optic papilla portion is included in the image. If the portion information detection unit 251 determines that the optic papilla portion is included in the image (YES in step S9), the processing proceeds to step S10. In step S10, the image generation unit 252 changes the tone curve so that an inclination of the tone curve corresponding to the bright portion is less steep. In step S9, if the portion information detection unit 251 determines that the optic papilla portion is not included in the image (NO in step S9), the processing proceeds to step S11. In step S11, the image generation unit 252 does not change the tone curve.

Figure 7A:
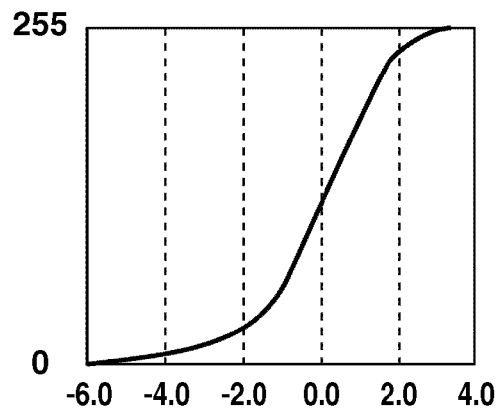
FIGS. 7A to 7C illustrate tone curves according to the first exemplary embodiment.
Figure 7B:
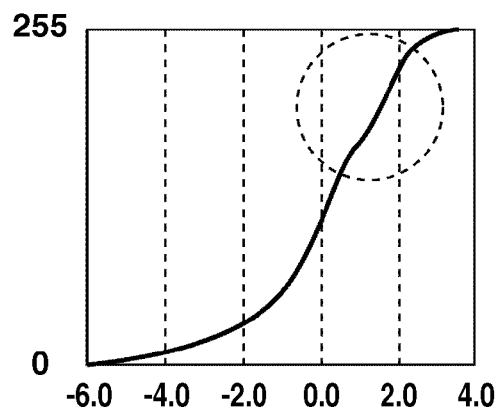
Figure 7C:
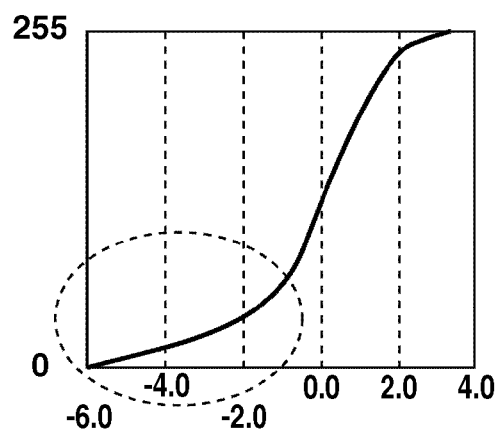

FIG. 7A illustrates an original tone curve. FIG. 7B illustrates a tone curve which is changed so that the inclination corresponding to the bright portion is less steep. FIG. 7C illustrates a tone curve which is changed so that the inclination corresponding to the dark portion is steeper.

When the processing in step S10 or step S11 is completed, the processing proceeds to step S12. In step S12, the portion information detection unit 251 reads out the image temporarily stored in the recording unit 28 and determines whether a macular portion in included in the image.

If the macular portion is not included in the image (YES in step S12), the processing proceeds to step S13. In step S13, the image generation unit 252 changes the tone curve so that the inclination of the tone curve corresponding to the dark portion is steeper. On the other hand, if the macular portion is not included in the image (NO in step S12), the processing proceeds to step S14. In step S14, the image generation unit 252 does not change the tone curve.

When the processing in step S13 or step S14 is completed, the processing proceeds to step S15. In step S15, the unprocessed image which has been temporarily stored in the recording unit 28 is read out. Then, the image generation unit 252 changes the gradation of the image according to the tone curve determined in steps S10, S11, S13 or S14. Alternatively, the image generation unit 252 generates a Joint Photographic Experts Group (JPEG) image according to the determined tone curve.

Now, a method for detecting the optic papilla portion of the fundus Er of the subject's eye E performed in step S9 and a method for detecting the macular portion of the fundus Er of the subject's eye E performed in step S12 will be described. In step S8, from the fundus image data temporarily stored in the recording unit 28, an 8-bit (0 to 255) image with an average value of all the pixels at 120, which is substantially the median value, is generated.

Since the optic papilla portion is generally the brightest portion in the fundus image, the portion information detection unit 251 considers a portion of a pixel value of 200 or more to be a candidate optic papilla portion, for example. In determining the optic papilla portion, the portion information detection unit 251 also considers a size and a shape of the portion. Although there are differences in the size of the optic papilla among individuals, generally, the area of the optic papilla is 0.8 $mm^2$ to 6 $mm^2$. Further, the shape of the optic papilla has a substantially elliptical shape. According to the present exemplary embodiment, a roughly elliptical and continuous portion whose pixel value is 200 or more and the size is 0.4 $mm^2$ or more is determined to be the optic papilla portion.

Since the macular portion is generally the darkest portion in the fundus image, the portion information detection unit 251 considers a portion of a pixel value of 50 or less to be a candidate macular portion, for example. In determining the macular portion, the portion information detection unit 251 also considers a size and a shape of the portion. Generally, a central fovea of a macular portion is circular and approximately 1.5 mm in diameter. According to the present exemplary embodiment, a roughly circular and continuous portion with a pixel value of 50 or less and approximately 1.0 mm or greater in diameter is determined to be the macular portion.

Figure 8A:
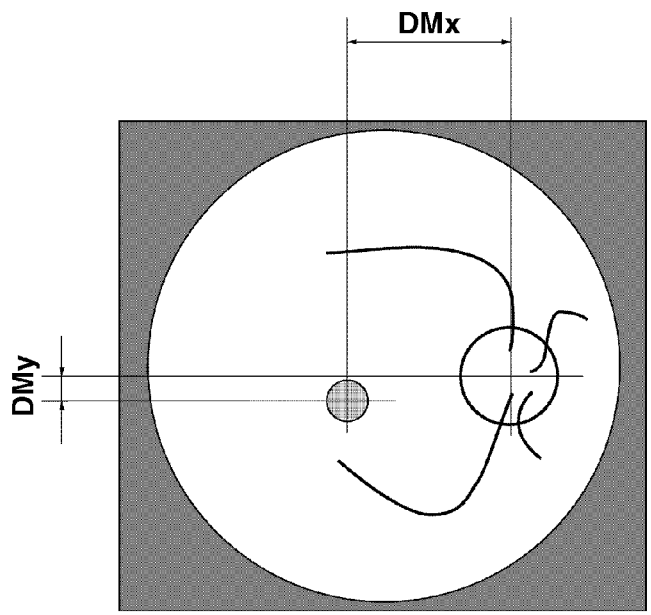
FIG. 8A illustrates a positional relation between an optic papilla portion and a macular portion in a fundus image.
Figure 8B:
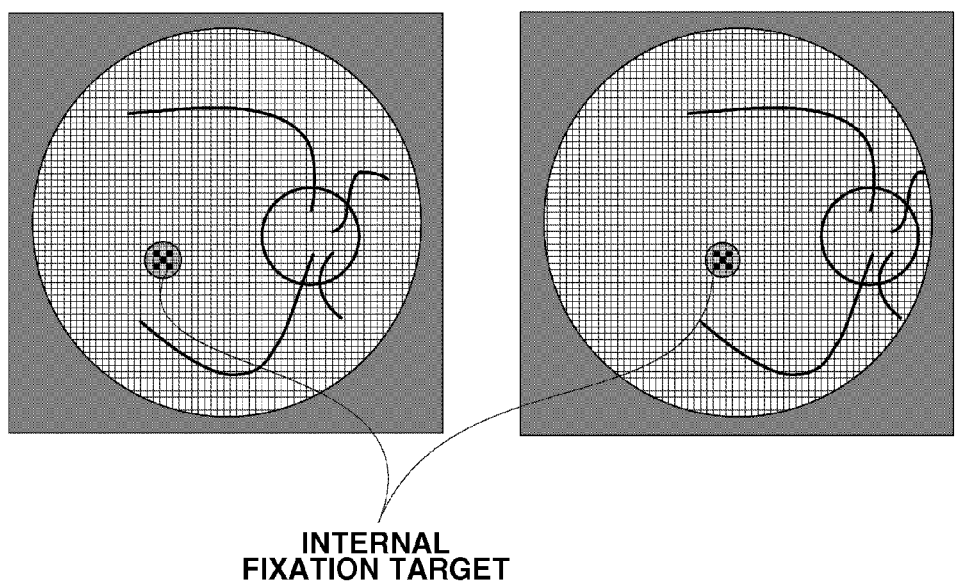
FIG. 8B illustrates a positional relation between a macular portion and an internal fixation target in a fundus image.

The optic papilla portion may also be detected by using, for example, an internal fixation light position and information about whether the subject's eye is right or left. Generally, a central fovea which is a center of a macula is located at a position where DMx is approximately 4 mm to the direction of the ear and DMy is approximately 0.8 mm downward from the center of the optic papilla portion. FIG. 8A illustrates a positional relation between the optic papilla and the macula of a right eye. As illustrated in FIG. 8B, there is the following relation.

The position of the internal fixation target≈The position of the macular portion (the central fovea)

Thus, if information about the position of the internal fixation target and information about whether the subject's eye is right or left are obtained, the position of the optic papilla portion can be determined from the DMx and DMy values. Accordingly, whether an optic papilla portion or a macular portion is included in the eye fundus image can be determined.

As described above, the quick return mirror 21 is a dichroic mirror. The quick return mirror 21 transmits infrared light and reflects visible light. The fundus image illuminated by the observation light source 1 is formed on the image sensor 19 and photoelectric conversion is performed thereon. Then, according to the image signal processing unit 23, data is read out from the image sensor 19, and amplification and A/D conversion of the data is performed. Accordingly, digital image data is generated, and the data is input in the calculation unit 25 as an unprocessed image.

According to the first exemplary embodiment, the presence or absence of the optic papilla portion or the macular portion is detected from a captured image of the eye fundus. However, the presence or absence of the optic papilla portion or the macular portion is detected from the eye fundus image observed by the operator, and then the tone curve which is applied to the captured image can also be changed according to the detected result.

Figure 10:
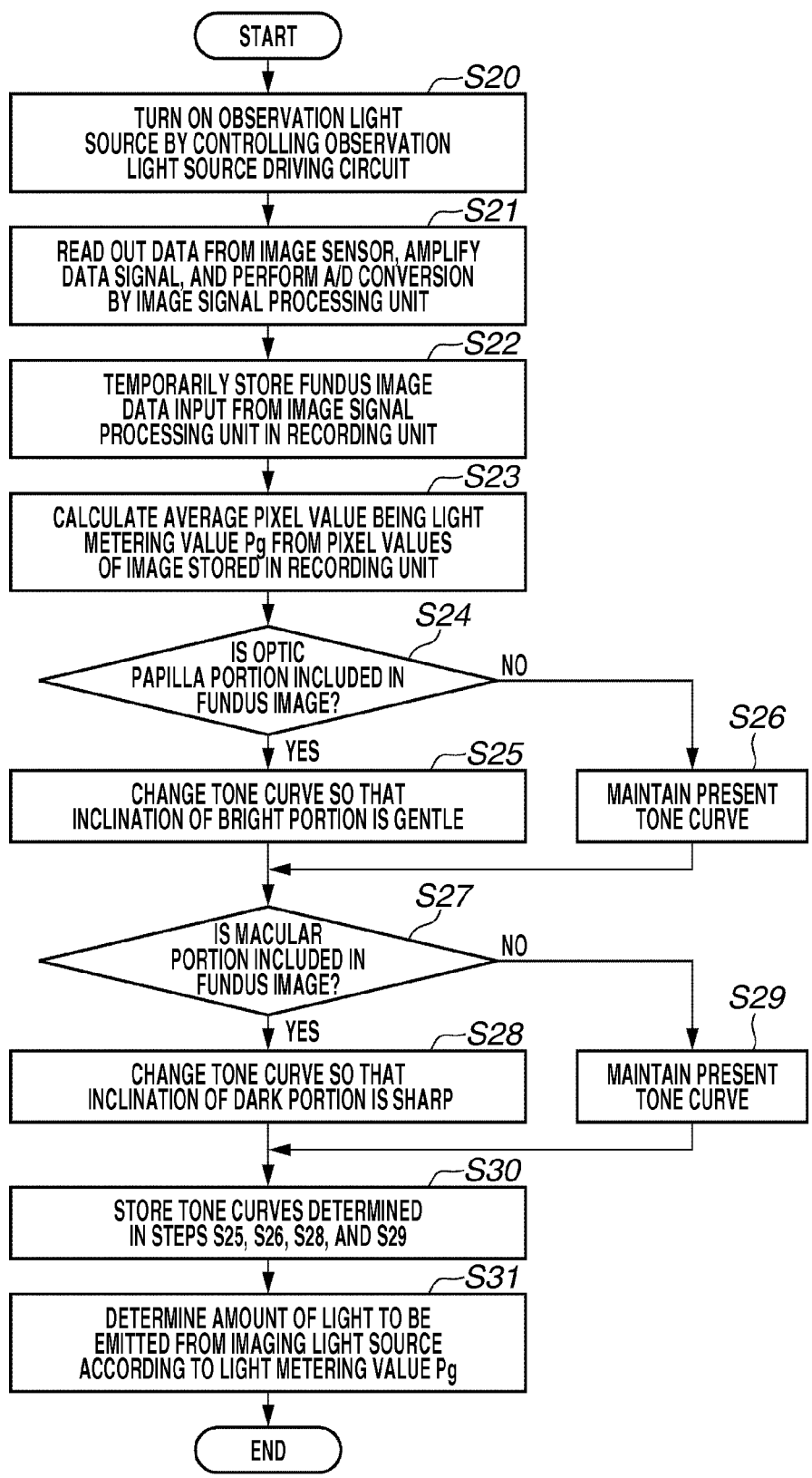
FIG. 10 is a flowchart illustrating an operation of a calculation unit according to a second exemplary embodiment of the present invention.

Next, a second exemplary embodiment will be described with reference to a flowchart illustrated in FIG. 10.

In step S20, the calculation unit 25 turns on the observation light source 1 by controlling the observation light source driving circuit 27. In step S21, the image signal processing unit 23 reads out data from the image sensor 19, amplifies the data, and performs A/D conversion of the amplified data. Then, the obtained data is input in the calculation unit 25 as the digital fundus image data. In step S22, the digital fundus image data is temporarily stored in the recording unit 28.

In step S23, the image data temporarily stored in the recording unit 28 is read out and an average pixel value of the digital image data is calculated from the image data as a light metering value Pg. In step S24, the portion information detection unit 251 detects whether an optic papilla portion is included in the image.

If the portion information detection unit 251 determines that the optic papilla portion is included in the image (YES in step S24), the processing proceeds to step S25. In step S25, the image generation unit 252 changes the tone curve so that the inclination of the tone curve corresponding to the bright portion is less steep. In step S24, if the portion information detection unit 251 determines that the optic papilla portion is not included in the image (NO in step S24), the processing proceeds to step S26. In step S26, the image generation unit 252 does not change the tone curve.

When the processing in step S25 or step S26 is completed, the processing proceeds to step S27. In step S27, the portion information detection unit 251 reads out the image temporarily stored in the recording unit 28, and detects whether a macular portion is included in the image.

If the portion information detection unit 251 determines that the macular portion is included in the image (YES in step S27), the processing proceeds to step S28. In step S28, the image generation unit 252 changes the tone curve so that the inclination of the dark portion is steeper. In step S27, if the portion information detection unit 251 determines that the macular portion is not included in the image (NO in step S27), then the processing proceeds to step S29. In step S29, the image generation unit 252 does not change the tone curve.

When the processing in step S28 or step S29 is completed, the processing proceeds to step S30. The tone curve determined in steps S25, S26, S28, and S29 is stored in the recording unit 28. The tone curve is used when a JPEG image is generated from the unprocessed image at the time the image is captured.

In step S31, the amount of light emitted from the photographing light source 2 is calculated and determined based on the light metering value Pg.

The detection method of the optic papilla portion and the macular portion is similar to the method described according to the first exemplary embodiment.

FIG. 9 is a flowchart illustrating an operation of a calculation unit 25 according to a third exemplary embodiment of the present invention. The operation is described in detail below with reference to the flowchart in FIG. 9.

In step S40, according to a stage position detection switch (not shown), the right-and-left detection unit 253 detects which of the eyes, the right or the left, is the subject eye. In step S41, the portion information detection unit 251 detects an index lighting position of the internal fixation target 29.

The portion information detection unit 251 determines whether a macular portion is included in the image according to an output of the right-and-left detection unit 253 and the index lighting position or the index projection position of the internal fixation target 29. Then, the image generation unit 252 generates an image using a tone curve which is generated according to the output from the portion information detection unit 251.

Figure 5B:
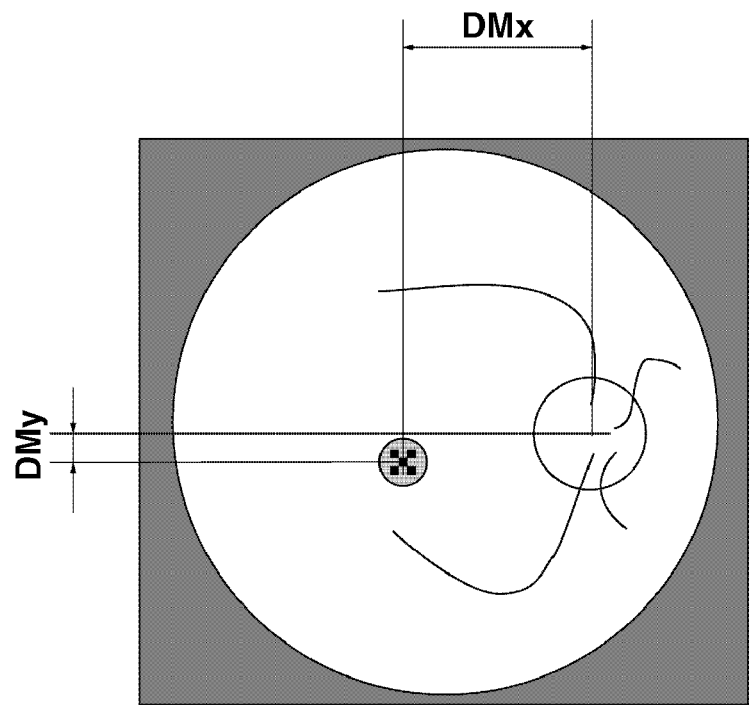
FIG. 5B illustrates a positional relation between a lighting position of an internal fixation target and positions of a macular portion and an optic papilla portion in a fundus image.

As illustrated in FIG. 5B, the index projection position of the internal fixation target 29 substantially coincides with the position of the macular portion. In step S42, the right-and-left detection unit 253 determines whether the subject's eye is the right eye or the left eye. If the subject's eye is determined to be the right eye (YES in step S42), the processing proceeds to step S43.

In step S43, the portion information detection unit 251 determines whether the index projection position of the internal fixation target 29 is in a range R1 illustrated in FIG. 3A. If the portion information detection unit 251 determines that the index projection position is in the range R1 (YES in step S43), the processing proceeds to step S45. In step S45, the image generation unit 252 changes the tone curve so that the inclination of the tone curve corresponding to the bright portion is less steep. In step S43, if the portion information detection unit 251 determines that the index lighting position of the internal fixation target 29 is not in the range R1 illustrated in FIG. 3A (NO in step S43), the processing proceeds to step S46. In step S46, the image generation unit 252 does not change the tone curve.

When the processing in step S45 or step S46 is completed, the processing proceeds to step S49. In step S49, the portion information detection unit 251 determines whether the index projection position of the internal fixation target 29 is in a range R1+range R2 illustrated in FIG. 3A. If the index projection position is in the range R1+range R2 (YES in step S49), the processing proceeds to step S51. In step S51, the image generation unit 252 changes the tone curve so that the inclination of the tone curve corresponding to the dark portion is steeper. In step S49, if the portion information detection unit 251 determines that the index lighting position of the internal fixation target 29 is not in the range R1+range R2 illustrated in FIG. 3A (NO in step S49), the processing proceeds to step S52. In step S52, the image generation unit 252 does not change the tone curve.

In step S42, if the right-and-left detection unit 253 determines that the subject's eye is the left eye (NO in step S42), the processing proceeds to step S44.

In step S44, the portion information detection unit 251 determines whether the lighting index of the internal fixation target 29 is in a range L1 illustrated in FIG. 3B. If the lighting index is in the range L1 (YES in step S44), then the processing proceeds to step S47. In step S47, the image generation unit 252 changes the tone curve so that the inclination of the tone curve corresponding to the bright portion is less steep. In step S44, if the portion information detection unit 251 determines that the lighting index of the internal fixation target 29 is not in the range L1 illustrated in FIG. 3B (NO in step S44), the processing proceeds to step S48. In step S48, the image generation unit 252 does not change the tone curve.

When the processing in step S47 or step S48 is completed, the processing proceeds to step S50. In step S50, the portion information detection unit 251 determines whether the index lighting position of the internal fixation target 29 is in a range L1+range L2 illustrated in FIG. 3B. If the index projection position is in the range L1+range L2 (YES in step S50), the processing proceeds to step S53. In step S53, the image generation unit 252 changes the tone curve so that the inclination of the tone curve corresponding to the dark portion is steeper. In step S50, if the portion information detection unit 251 determines that the index lighting position of the internal fixation target 29 is not in the range L1+range L2 illustrated in FIG. 3B (NO in step S50), the processing proceeds to step S54. In step S54, the image generation unit 252 does not change the tone curve.

When the processing in steps S51, S52, S53, and S54 is completed, the processing proceeds to step S55. In step S55, the tone curve determined in steps S45, S46, S47, S48, S51, S52, S53, and S54 is temporarily stored in the recording unit 28.

As described above, according to the above described exemplary embodiments, the tone curve is changed according to the information of each fundus portion. Then, an image is generated from the unprocessed image by using the tone curve. Accordingly, an eye fundus image with appropriate brightness can be obtained. More precisely, the brightness of each fundus portion of the eye fundus image is adjusted to appropriate brightness.

Further, whether an optic papilla portion is included in the eye fundus image is detected, and the tone curve is changed according to whether the optic papilla portion is included in the image. Since the image is generated from the unprocessed image using the tone curve, an eye fundus image with appropriate brightness in both of the optic papilla portion and other portions can be acquired.

Further, whether a macular portion is included in the eye fundus image is detected, and the tone curve is changed according to whether the macular portion is included in the image. Since the image is generated from the unprocessed image using the tone curve, an eye fundus image with appropriate brightness in both of the macular portion and other portions can be acquired.

Further, since a portion in the image data with a predetermined luminance value or more is determined as the optic papilla portion, the optic papilla portion is reliably detected.

Furthermore, since a portion in the image data with a predetermined luminance value or less is determined as the macular portion, the macular portion can be reliably detected.

Additionally, according to the above described exemplary embodiments, since the optic papilla portion and the macular portion are detected based on information about at least the position of the fixation target for guiding the fixation of the subject's eye or the detection result of whether the subject's eye is the right eye or not, the optic papilla portion and the macular portion can be reliably detected. Since a portion in the image data with a predetermined luminance value or less is determined as the macular portion, the optic papilla portion and the macular portion can be reliably detected.

Further, according to the above described exemplary embodiments, the optic papilla portion and the macular portion are detected with using the light metering unit that performs light metering of the exposure state of the fundus based on the fundus image which has been formed by illumination of observation light or photographing light. Therefore, a compact and inexpensive fundus camera that can capture an eye fundus image including both the optic papilla portion, or the macular portion and other portions with appropriate brightness can be provided.

Further, since an amount of the photographing light is adjusted based on the output of the light metering unit, a fundus image with appropriate exposure can be acquired.

According to the above described exemplary embodiments, the presence or absence of the optic papilla portion in the fundus image is detected and only an inclination of a portion of a tone curve corresponding to a predetermined luminance value or more is changed according to the presence or absence of the optic papilla portion, and an image is generated from the unprocessed image using the tone curve. Thus, an eye fundus image including both the optic papilla portion and portions other than the optic papilla portion in appropriate brightness can be provided.

Further, since an inclination of a portion of the tone curve corresponding to a predetermined luminance value or less is changed according to the presence or absence of the macular portion, an eye fundus image including both the macular portion and portions other than the macular portion in appropriate brightness can be provided.

Further, according to the above described exemplary embodiments, the tone curve is changed based on the position of the fixation target and whether the right eye or the left eye is detected as the subject's eye, and an image is generated from the unprocessed image using the obtained tone curve. Thus, an eye fundus image with appropriate brightness at each portion of the fundus can be provided.

If the position of the fixation target is in a predetermined range of the fundus image, only the inclination of the tone curve corresponding to the bright portion with a predetermined luminance value or more is changed. Then, an image is generated from the unprocessed image using the tone curve.

Thus, an eye fundus image with appropriate brightness at each portion of the fundus can be provided.

Further, if the position of the fixation target is in the fundus image, only the inclination of the tone curve corresponding to the dark portion with a predetermined luminance value or less is changed. Then, an image is generated from the unprocessed image using the tone curve. Thus, an eye fundus image with appropriate brightness at each portion of the fundus can be provided.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-285764 filed Dec. 16, 2009, which is hereby incorporated by reference herein in its entirety.

What is claimed is:

1. An ophthalmic system comprising:
an imaging unit configured to capture a fundus image formed via a photographic optical system;
a portion information detection unit configured to detect whether an area corresponding to at least an optic papilla portion or a macular portion is included in the fundus image acquired from the imaging unit; and
an image generation unit configured to generate an image according to a tone curve which is changed according to a result of a detection performed by the portion information detection unit of the fundus image.

2. The ophthalmic system according to claim 1, wherein the portion information detection unit detects a portion with a predetermined luminance value or more of the image data as an area corresponding to the optic papilla portion or detects a portion with a predetermined luminance or lower of the image data as an area corresponding to the macular portion.

3. The ophthalmic system according to claim 1, further comprising a light metering unit configured to perform light metering of an exposure state of a fundus based on the fundus image captured by the imaging unit,
wherein the portion information detection unit detects an area corresponding to at least an optic papilla portion or a macular portion of the fundus image based on an output of the light metering unit.

4. The ophthalmic system according to claim 3, wherein an amount of light emitted from an illumination unit configured to illuminate the fundus when an image is captured is adjusted based on an output of the light metering unit.

5. An ophthalmic system comprising:
an imaging unit configured to capture a fundus image formed via a photographic optical system;
a portion information detection unit configured to detect information about a predetermined portion of a fundus from image data acquired from the imaging unit;
an image generation unit configured to generate an image according to a tone curve which is changed according to a result of a detection performed by the portion information detection unit of the fundus image;
a fixation target configured to turn on an index used for guiding fixation of a subject's eye, and
a right-and-left detection unit configured to detect whether the subject's eye is a left eye or a right eye,
wherein the portion information detection unit detects an area corresponding to at least an optic papilla portion or a macular portion from the fundus image using at least a position of the fixation target or a detection result of the right-and-left detection unit.

6. An ophthalmic system comprising:
an imaging unit configured to capture a fundus image formed via a photographic optical system;
a portion information detection unit configured to detect information about a predetermined portion of a fundus from image data acquired from the imaging unit;
an image generation unit configured to generate an image according to a tone curve which is changed according to a result of a detection performed by the portion information detection unit of the fundus image;
wherein the image generation unit changes, among inclination pitches of the tone curve of an area corresponding to an optic papilla in the fundus image, the inclination pitch applied to a portion with a predetermined luminance value or more such that the inclination pitch is less steep, and among inclination pitches of the tone curve of an area corresponding to a macular portion in the fundus image, the inclination pitch applied to a portion with a predetermined luminance value or less such that the inclination pitch is steeper.

7. An ophthalmic system comprising:
an imaging unit configured to capture a fundus image formed via a photographic optical system;
a fixation target configured to turn on an index used for guiding fixation of a subject's eye;
a portion information detection unit configured to detect an area corresponding to a macular portion of the fundus image from a projection position of the index on a fundus of the subject's eye; and
an image generation unit configured to generate an image according to a tone curve which is changed according to a result of a detection performed by the portion information detection unit of the fundus image.

8. An ophthalmic system comprising:
an imaging unit configured to capture a fundus image formed via a photographic optical system;
a fixation target configured to turn on an index used for guiding fixation of a subject's eye;
a portion information detection unit configured to detect an area corresponding to a macular portion of the fundus image from a projection position of the index on a fundus of the subject's eye;
an image generation unit configured to generate an image according to a tone curve which is changed according to a result of a detection performed by the portion information detection unit of the fundus image; and
a right-and-left detection unit configured to detect whether the subject's eye is a left eye or a right eye,
wherein the portion information detection unit detects an area corresponding to an optic papilla in the fundus image using the projection position and an output of the right-and-left detection unit,
wherein the image generation unit changes, among inclination pitches of the tone curve of an area corresponding to the optic papilla, the inclination pitch applied to a portion with a predetermined luminance value or more such that the inclination pitch is less steep, and among inclination pitches of the tone curve of an area corresponding to the macular portion, the inclination pitch applied to a portion with a predetermined luminance value or less such that the inclination pitch is steeper.

9. An ophthalmologic image processing apparatus comprising:
a portion information detection unit configured to detect an area corresponding to at least an optic papilla portion of a macular portion of a first fundus image from at least first data relating to a position of a fixation target that turns on an index used for guiding fixation of a subject's eye included in the first fundus image or second data relating to a right eye or a left eye of the subject's eye included in a first fundus image; and
an image generation unit configured to generate a second fundus image according to a tone curve which is changed according to a detection result of the portion information detection unit of the first fundus image data.

10. An ophthalmologic image processing apparatus comprising:
a portion information detection unit configured to detect information about a predetermined portion of a fundus from a first fundus image data; and
an image generation unit configured to generate a second fundus image according to a tone curve which is changed according to a detection result of the portion information detection unit of the first fundus image data;
wherein the image generation unit changes, among inclination pitches of the tone curve of an area corresponding to an optic papilla of the first fundus image, the inclination pitch applied to a portion with a predetermined luminance value or more such that the inclination pitch is less steep, and among inclination pitches of the tone curve of an area corresponding to a macular portion of the first fundus image, the inclination pitch applied to a portion with a predetermined luminance value or less such that the inclination pitch is steeper.

* * * * *